United States Patent
Noda

(10) Patent No.: US 12,303,842 B2
(45) Date of Patent: May 20, 2025

(54) ZEOLITE MEMBRANE COMPLEX, SEPARATION APPARATUS, SEPARATION METHOD AND METHOD OF PRODUCING ZEOLITE MEMBRANE COMPLEX

(71) Applicant: NGK INSULATORS, LTD., Nagoya (JP)

(72) Inventor: Kenichi Noda, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 241 days.

(21) Appl. No.: 17/929,778

(22) Filed: Sep. 6, 2022

(65) Prior Publication Data
US 2022/0410083 A1 Dec. 29, 2022

Related U.S. Application Data

(63) Continuation of application No. PCT/JP2020/046947, filed on Dec. 16, 2020.

(30) Foreign Application Priority Data

Mar. 24, 2020 (WO) .................. PCT/JP2020/012910

(51) Int. Cl.
*B01D 71/02* (2006.01)
*B01D 53/22* (2006.01)
(Continued)

(52) U.S. Cl.
CPC ....... *B01D 71/0281* (2022.08); *B01D 53/228* (2013.01); *B01D 67/0051* (2013.01);
(Continued)

(58) Field of Classification Search
CPC .. B01D 71/02; B01D 71/0281; B01D 53/228; B01D 67/0051; B01D 2323/12;
(Continued)

(56) References Cited

U.S. PATENT DOCUMENTS

| | | | |
|---|---|---|---|
| 5,443,812 A | 8/1995 | Nakajima et al. | |
| 2008/0039554 A1* | 2/2008 | Liu | B01D 67/00793 523/310 |
| 2020/0399136 A1* | 12/2020 | Anthonis | C01B 37/02 |

FOREIGN PATENT DOCUMENTS

| | | |
|---|---|---|
| EP | 1 647 531 A1 | 4/2006 |
| JP | H03-242317 A | 10/1991 |

(Continued)

OTHER PUBLICATIONS

English translation of the International Preliminary Report on Patentability (Chapter I) dated Oct. 6, 2022 (Application No. PCT/JP2020/046947).

(Continued)

*Primary Examiner* — In Suk C Bullock
*Assistant Examiner* — Jason Y Chong
(74) *Attorney, Agent, or Firm* — BURR PATENT LAW, PLLC

(57) ABSTRACT

A zeolite membrane complex includes a porous support, and a zeolite membrane formed on the support and composed of an 8-membered ring zeolite. The zeolite membrane is selectively permeable to hydrogen sulfide rather than nitrogen for a gas containing nitrogen and hydrogen sulfide.

14 Claims, 3 Drawing Sheets

(51) Int. Cl.
  *B01D 67/00* (2006.01)
  *B01D 69/02* (2006.01)
  *C07C 7/144* (2006.01)

(52) U.S. Cl.
  CPC .............. *B01D 71/02* (2013.01); *C07C 7/144* (2013.01); *B01D 2323/12* (2013.01); *B01D 2323/24* (2013.01); *B01D 2323/48* (2013.01)

(58) Field of Classification Search
  CPC ............ B01D 2323/24; B01D 2323/48; B01D 2257/304; B01D 69/02; C07C 7/144
  See application file for complete search history.

(56) References Cited

FOREIGN PATENT DOCUMENTS

| | | |
|---|---|---|
| JP | 2006-112488 A | 4/2006 |
| JP | 2007-268463 A | 10/2007 |
| JP | 2014046267 A * | 3/2014 |
| JP | 2016-506293 A | 3/2016 |
| JP | 2016-107259 A | 6/2016 |
| JP | 2019-171234 A | 10/2019 |
| WO | 2014/088756 A1 | 6/2014 |

OTHER PUBLICATIONS

"Development of System Recovering Methane from Biogas Using DDR-Type Zeolite Membrane," by Tomohiro Takemi and 3 other members, the 31st annual meeting of Niigata conference, Kanto Branch of JSCE, 2014, pp. 484-485 (with English concise explanation of the relevance).

International Search Report and Written Opinion dated Feb. 22, 2021 (Application No. PCT/JP2020/046947).

International Bureau of WIPO—Informal Comments (with English translation) dated May 25, 2021 (Application No. PCT/JP2020/0446947).

* cited by examiner

ZEOLITE MEMBRANE COMPLEX, SEPARATION APPARATUS, SEPARATION METHOD AND METHOD OF PRODUCING ZEOLITE MEMBRANE COMPLEX

CROSS-REFERENCE TO RELATED APPLICATION

The present application is a continuation application of International Application No. PCT/JP2020/046947 filed on Dec. 16, 2020, which claims priority to International Application No. PCT/JP2020/012910 filed on Mar. 24, 2020. The contents of these applications are incorporated herein by reference in their entirety.

TECHNICAL FIELD

The present invention relates to a zeolite membrane complex, and a separation technique using the zeolite membrane complex.

BACKGROUND ART

Japanese Patent Application Laid-Open No. 2006-112488 (Document 1), and "Development of System for Recovering Methane from Biogas Using DDR-type Zeolite Membrane" by Tomohiro Takemi and other 3 members, the 31st annual meeting of Niigata conference, Kanto branch of JSCE, 2014, pp. 484-485 (Document 2) disclose apparatuses for separating methane from biogas such as digestion gas using DDR-type zeolite membranes. Since biogas contains hydrogen sulfide in addition to methane and carbon dioxide, the sulfur compound is preliminarily removed from the biogas using desulfurization equipment in Documents 1 and 2.

Japanese Patent Application Laid-Open No. 2014-46267 (Document 3) discloses a method for separating hydrogen sulfide from a mixed gas containing hydrogen sulfide using an 8-membered ring zeolite membrane (i.e., a zeolite membrane containing a zeolite structure with 8-membered oxygen rings). Japanese Patent Application Laid-Open No. 2019-171234 (Document 4) discloses a method of recovering the separation performance of a zeolite membrane for hydrogen sulfide separation, and in the method, the zeolite membrane with reduced separation performance is heated at a temperature between 30° C. and 500° C. under vacuum to remove the sulfur content from the zeolite.

It is conceivable that after long-time use of the zeolite membrane in Document 3, hydrogen sulfide accumulates in the membrane to thereby decrease the permeance of hydrogen sulfide as described in Document 2, and the separation performance of the zeolite membrane is reduced. In the case where a desulfurization equipment for removing hydrogen sulfide from the mixed gas is provided, the cost of separating hydrogen sulfide increases. When employing the technique of Document 4 where the separation performance of zeolite membrane is recovered by heating, the cost of separating hydrogen sulfide increases and the procedures in the separation process are complicated. Thus, there is a need for a zeolite membrane that is stably permeable to hydrogen sulfide, even when the concentration of hydrogen sulfide is high.

SUMMARY OF THE INVENTION

The present invention is intended for a zeolite membrane complex, and it is an object of the present invention to provide a zeolite membrane complex including a zeolite membrane that is stably permeable to hydrogen sulfide.

The zeolite membrane complex according to the present invention includes a porous support, and a zeolite membrane provided on the support, the zeolite membrane being composed of an 8-membered ring zeolite. The zeolite membrane contains protons, and the zeolite membrane is selectively permeable to hydrogen sulfide rather than nitrogen for a gas containing nitrogen and hydrogen sulfide.

According to the present invention, it is possible to provide a zeolite membrane complex that is stably permeable to hydrogen sulfide.

Preferably, in temperature-programmed desorption of ammonia measurement for the zeolite membrane, an amount of desorbed ammonia in a peak temperature range in which the amount of desorbed ammonia is maximum is 1 μmol/cm$^3$ or more.

Preferably, in the zeolite membrane, a ratio of alkali metal atoms to oxygen atoms is 1 atm % or less.

The present invention is also intended for a separation apparatus. The separation apparatus according to the present invention includes the above zeolite membrane complex, and a supply part for supplying a mixed gas containing at least hydrogen sulfide to the zeolite membrane complex.

Preferably, the mixed gas contains hydrocarbon.

Preferably, a concentration of hydrogen sulfide in the mixed gas is 3 mol % or more.

The present invention is also intended for a separation method. The separation method according to the present invention includes preparing the above zeolite membrane complex, and supplying a mixed gas containing at least hydrogen sulfide to the zeolite membrane complex.

Preferably, the mixed gas contains hydrocarbon.

Preferably, a concentration of hydrogen sulfide in the mixed gas is 3 mol % or more.

The present invention is also intended for a method of producing a zeolite membrane complex. The method of producing a zeolite membrane complex according to the present invention includes forming a zeolite membrane on a porous support with use of a starting material solution containing a structure-directing agent, the zeolite membrane being composed of an 8-membered ring zeolite, removing the structure-directing agent from the zeolite membrane, and immersing the zeolite membrane in a treatment solution for one hour or more to obtain the zeolite membrane which contains protons and which is selectively permeable to hydrogen sulfide rather than nitrogen for a gas containing nitrogen and hydrogen sulfide, the treatment solution being alkaline and substantially free of ammonium ions.

Preferably, a pH of the treatment solution is in the range of 9.5 to 12.

Preferably, a concentration of alkali metal ions in the treatment solution is 0.1 mol/L or less.

Preferably, the treatment solution contains at least one of silicon and aluminum.

In this case, preferably, a total concentration of silicon and aluminum atoms in the treatment solution is 0.001 mol/L or more, and the total concentration is less than the concentration in the starting material solution and 1 mol/L or less.

These and other objects, features, aspects and advantages of the present invention will become more apparent from the following detailed description of the present invention when taken in conjunction with the accompanying drawings.

DESCRIPTION OF EMBODIMENTS

Figure 1:
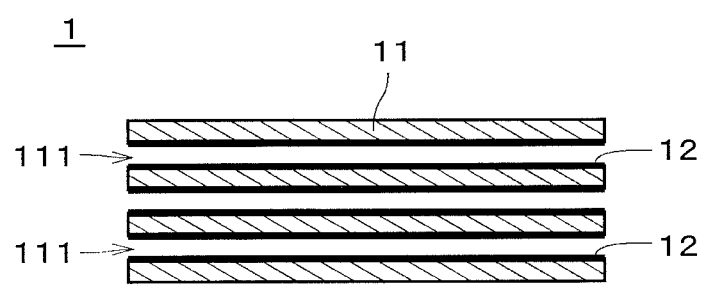
FIG. 1 is a sectional view of a zeolite membrane complex.
Figure 2:
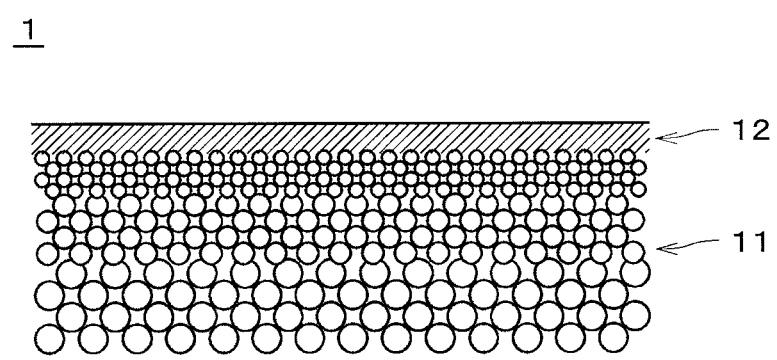
FIG. 2 is a sectional view illustrating part of the zeolite membrane complex in enlarged dimension.

FIG. 1 is a sectional view of a zeolite membrane complex 1. FIG. 2 is a sectional view illustrating part of the zeolite membrane complex 1 in enlarged dimension. The zeolite membrane complex 1 includes a porous support 11 and a zeolite membrane 12 provided on the support 11. The zeolite membrane 12 refers to at least a zeolite formed into a membrane on a surface of the support 11, and does not include zeolite particles that are merely dispersed in an organic membrane. In FIG. 1, the zeolite membrane 12 is illustrated with bold lines. In FIG. 2, the zeolite membrane 12 is indicated by hatching. In FIG. 2, the thickness of the zeolite membrane 12 is illustrated thicker than the actual thickness.

The support 11 is a porous member permeable to gases and liquids. In the example illustrated in FIG. 1, the support 11 is a monolith support obtained by forming a plurality of through holes 111, each extending in a longitudinal direction (i.e., a left-right direction in FIG. 1), in an integral columnar body that is molded integrally. In the example illustrated in FIG. 1, the support 11 has a substantially circular columnar shape. Each through hole 111 (i.e., cell) has, for example, a substantially circular section perpendicular to the longitudinal direction. In FIG. 1, the through holes 111 are illustrated as having a greater diameter than the actual diameter, and a smaller number of through holes 111 than the actual number. The zeolite membrane 12 is formed on the inner surfaces of the through holes 111 and covers substantially the entire inner surfaces of the through holes 111.

The support 11 has a length (i.e., length in the left-right direction in FIG. 1) of, for example, 10 cm to 200 cm. The support 11 has an outer diameter of, for example, 0.5 cm to 30 cm. The distance between the central axes of each pair of adjacent through holes 111 is, for example, in the range of 0.3 mm to 10 mm. The surface roughness (Ra) of the support 11 is, for example, in the range of 0.1 µm to 5.0 µm and preferably in the range of 0.2 µm to 2.0 µm. Alternatively, the support 11 may have a different shape such as a honeycomb shape, a flat plate shape, a tubular shape, a circular cylindrical shape, a circular columnar shape, or a polygonal prism shape. When having a tubular shape or a circular cylindrical shape, the support 11 has a thickness of, for example, 0.1 mm to 10 mm.

Various substances (e.g., a ceramic or a metal) may be employed as the material for the support 11 as long as they have chemical stability in the step of forming the zeolite membrane 12 on the surface. In the present embodiment, the support 11 is formed of a ceramic sintered compact. Examples of the ceramic sintered compact to be selected as the material for the support 11 include alumina, silica, mullite, zirconia, titania, yttria, silicon nitride, and silicon carbide. In the present embodiment, the support 11 contains at least one of alumina, silica, and mullite.

The support 11 may contain an inorganic binder. The inorganic binder may be at least one of titania, mullite, easily sinterable alumina, silica, glass frit, clay minerals, and easily sinterable cordierite.

The support 11 has a mean pore diameter of, for example, 0.01 µm to 70 µm and preferably 0.05 µm to 25 µm. A portion of the support 11 that is located in the vicinity of the surface where the zeolite membrane 12 is formed has a mean pore diameter of 0.01 µm to 1 µm, and preferably 0.05 µm to 0.5 µm. As to a pore size distribution of the support 11 as a whole including the surface and inside of the support 11, D5 is, for example, in the range of 0.01 µm to 50 µm, D50 is, for example, in the range of 0.05 µm to 70 µm, and D95 is, for example, in the range of 0.1 µm to 2000 µm. The portion of the support 11 that is located in the vicinity of the surface where the zeolite membrane 12 is formed has a porosity of, for example, 20% to 60%.

The support 11 has, for example, a multilayer structure in which a plurality of layers having different mean pore diameters are laminated one above another in the thickness direction. The mean pore diameter and sintered particle diameter of a surface layer that includes the surface where the zeolite membrane 12 is formed are smaller than mean pore diameters and sintered particle diameters of other layers different from the surface layer. The surface layer of the support 11 has a mean pore diameter of, for example, 0.01 µm to 1 µm, and preferably 0.05 µm to 0.5 µm. When the support 11 has a multilayer structure, the material for each layer may be any of the materials described above. The materials for the plurality of layers, which form the multilayer structure, may be the same material, or may be different materials.

The zeolite membrane 12 is a porous membrane having micropores. The zeolite membrane 12 can be used as a separation membrane to separate a specific substance from a mixed substance containing a plurality of types of substances by using molecular sieving function. The zeolite membrane 12 is less permeable to other substances than to the specific substance. In other words, the amount by which the other substances permeate through the zeolite membrane 12 is smaller than the amount by which the aforementioned specific substance permeates through the zeolite membrane 12. As described later, the zeolite membrane 12 is selectively permeable to hydrogen sulfide ($H_2S$) rather than nitrogen ($N_2$) for a gas containing nitrogen and hydrogen sulfide.

The zeolite membrane 12 has a thickness of, for example, 0.05 µm to 30 µm, preferably 0.1 µm to 20 µm, and more preferably 0.5 µm to 10 µm. Separation performance improves as the thickness of the zeolite membrane 12 increases. The permeance increases as the thickness of the zeolite membrane 12 decreases. The surface roughness (Ra) of the zeolite membrane 12 is, for example, 5 µm or less, preferably 2 µm or less, more preferably 1 µm or less, and yet more preferably 0.5 µm or less.

The maximum number of membered rings of the zeolite constituting the zeolite membrane 12 is 8. In other words, the zeolite membrane 12 is an 8-membered ring zeolite membrane composed of an 8-membered ring zeolite where the maximum number of membered rings is 8. The zeolite membrane 12 typically consists only of an 8-membered ring zeolite, but depending on the producing method or the like, a small amount (e.g., 1 mass % or less) of substances other than the 8-membered ring zeolite may be contained in the zeolite membrane 12.

The type of the zeolite constituting the zeolite membrane 12, is not particularly limited as long as it is an 8-membered ring zeolite, and the zeolite may, for example, be any of the followings: AEI-type, AFN-type, AFV-type, AFX-type, CHA-type, DDR-type, ERI-type, ETL-type, GIS-type, IHW-type, LEV-type, LTA-type, LTJ-type, RHO-type, and SAT-type. More preferably, the zeolite may, for example, be any of the followings: AEI-type, AFN-type, AFV-type, AFX-type, CHA-type, DDR-type, ERI-type, ETL-type, GIS-type, LEV-type, RHO-type, and SAT-type. The zeolite membrane 12 is composed of, for example, a DDR-type zeolite. In other words, the zeolite membrane 12 is a zeolite membrane composed of a zeolite having a framework type code "DDR" assigned by the International Zeolite Association.

In the present embodiment, the mean pore diameter of the zeolite is an arithmetic mean of the major and minor axes of 8-membered ring pore. The 8-membered ring pore refers to a micropore in which eight oxygen atoms exist in a portion where oxygen atoms and T atoms described later are bonded together to form a ring structure. If the zeolite has a plurality of types of 8-membered ring pores, the mean pore diameter of the zeolite is an arithmetic mean of the major and minor axes of all types of 8-membered ring pores. In this way, the mean pore diameter of the zeolite membrane is uniquely determined by the framework structure of the zeolite and obtained from the values presented in the "Database of Zeolite Structures" [online] by the International Zeolite Association on the Internet (URL:http://www.iza-structure-.org/databases/).

The mean pore diameter of the zeolite membrane 12 is, for example, greater than or equal to 0.2 nm and less than or equal to 0.5 nm, preferably greater than or equal to 0.3 nm and less than or equal to 0.5 nm. The mean pore diameter of the zeolite membrane 12 is smaller than the mean pore diameter of the portion of the support 11 which is located in the vicinity of the surface where the zeolite membrane 12 is formed. In the case where the zeolite membrane 12 is composed of a DDR-type zeolite, the zeolite constituting the zeolite membrane 12 has an intrinsic pore diameter of 0.36 nm×0.44 nm and a mean pore diameter of 0.40 nm.

The zeolite membrane 12 contains, for example, silicon (Si). For example, the zeolite membrane 12 may contain any two or more of Si, aluminum (Al), and phosphorus (P). In this case, the zeolite constituting the zeolite membrane 12 may, for example, be a zeolite in which atoms (T atoms) each located in the center of an oxygen tetrahedron ($TO_4$) of zeolite are composed of only Si or Si and Al; an AlPO-type zeolite in which T atoms are composed of Al and P; an SAPO-type zeolite in which T atoms are composed of Si, Al, and P; an MAPSO-type zeolite in which T atoms are composed of magnesium (Mg), Si, Al, and P; or a ZnAPSO-type zeolite in which T atoms are composed of zinc (Zn), Si, Al, and P. Some of the T atoms may be replaced by other elements.

When the zeolite membrane 12 contains Si atoms and Al atoms, the Si/Al ratio in the zeolite membrane 12 is, for example, one or more and a hundred thousand or less. The Si/Al ratio is preferably 5 or more, more preferably 20 or more, and yet more preferably 100 or more, and is preferably as high as possible. The Si/Al ratio in the zeolite membrane 12 may be adjusted by, for example, adjusting the composition ratio of Si source and Al source in a starting material solution described later. When the zeolite membrane 12 contains Al atoms and P atoms, the P/Al ratio in the zeolite membrane 12 is preferably 0.7 or more and 1.5 or less. The P/Al ratio in the zeolite membrane 12 may be adjusted by, for example, adjusting the composition ratio of P source and Al source in a starting material solution described later.

Preferably, the zeolite constituting the zeolite membrane 12 substantially contains no P as T atoms. In other words, it is preferable that the zeolite should substantially contain no P as framework elements. This makes it possible to increase the heat resistance of the zeolite membrane 12. Note that "substantially contain no P as framework elements" means that the percentage of P in all T atoms is 3 mol % or less.

The zeolite membrane 12 may contain a small amount of alkali metal. The alkali metal is, for example, sodium (Na) or potassium (K). The smaller the ratio of alkali metal atoms to oxygen atoms, the better the zeolite membrane 12. For example, the ratio is 1 atm % or less. The ratio is preferably 0.7 atm % or less, and more preferably 0.5 atm % or less. The ratio of alkali metal atoms (including alkali metal ions) to oxygen atoms is the atomic percentage obtained by (the number of alkali metal atoms)/(the number of oxygen atoms). For example, it can be measured by X-ray photoelectron spectroscopy (XPS). The measurement of composition of the zeolite membrane 12 by XPS may be performed after etching the membrane surface with argon by about 1 nm to eliminate the influence of surface contamination. If the zeolite membrane 12 contains a plurality of types of alkali metals, the above ratio is the ratio of the sum of the plurality of types of alkali metal atoms to oxygen atoms.

The zeolite membrane 12 may contain a small amount of a structure-directing agent (hereinafter, also referred to as an "SDA"). That is, the zeolite constituting the zeolite membrane 12 may contain SDA. SDA is utilized in the formation of zeolite membrane 12. As described later, the preferred zeolite membrane 12 contains little SDA.

The zeolite membrane 12 contains protons. When performing temperature-programmed desorption of ammonia measurement for the preferred zeolite membrane 12, an amount of desorbed ammonia in a peak temperature range is 1 $\mu mol/cm^3$ or more. The higher the proton concentration in the zeolite membrane 12, the higher the amount of desorbed ammonia in the peak temperature range in the temperature-programmed desorption of ammonia measurement. In the temperature-programmed desorption of ammonia measurement, ammonia is adsorbed in a cut piece of the zeolite membrane complex 1 which is cut into a predetermined size, the cut piece is subjected to steam treatment, and then the amount of ammonia desorbed at each temperature is measured while the zeolite membrane 12 is heated at 10° C./min. The steam treatment removes ammonia other than ammonia adsorbed to protons. The amount of desorbed ammonia in the peak temperature range described above is the amount of desorbed ammonia integrated over a range extending 50° C. at each side of the peak temperature (a width of 100° C.), the peak temperature being obtained as a temperature at which the amount of desorbed ammonia becomes maximum within the range of 300-550° C. The volume of the zeolite membrane 12 used for the temperature-programmed desorption of ammonia measurement is obtained by the product of the thickness of the zeolite membrane 12 (thickness of the zeolite membrane on the surface of the support 11) determined by an electron microscopy (SEM) or the like, and the area of the zeolite membrane 12 contained in the cut piece of the zeolite membrane complex 1. The amount of desorbed ammonia in the peak temperature range is preferably 1.5 $\mu mol/cm^3$ or more, and more preferably 2 $\mu mol/cm^3$ or more or more. The upper limit of desorbed ammonia in the peak temperature range is not limited, but is, for example, 100 $\mu mol/cm^3$.

The zeolite membrane 12 is selectively permeable to hydrogen sulfide rather than nitrogen for a gas containing nitrogen and hydrogen sulfide at a molar ratio of 1:1

(hereinafter, referred to as an "evaluation gas"). In other words, in the evaluation gas, the amount (the number of molecules) of hydrogen sulfide permeating through the zeolite membrane 12 is greater than the amount of nitrogen permeating through the zeolite membrane 12. Specifically, the evaluation gas at a temperature of 25° C. is supplied to the zeolite membrane 12 at a pressure of 0.9 MPa. For the permeate gas that permeates through the zeolite membrane 12 and flows out (at a pressure of about 0.1 MPa), the flow rate is measured by a mass flow meter and the composition is measured by gas chromatography. Then, on the basis of the flow rate and composition of the permeate gas, the permeance of each of hydrogen sulfide and nitrogen per unit membrane area and unit pressure difference is calculated. If the ratio of hydrogen sulfide permeance to nitrogen permeance (i.e., (hydrogen sulfide permeance)/(nitrogen permeance)) is greater than 1, it can be said that the zeolite membrane 12 is selectively permeable to hydrogen sulfide rather than nitrogen. The above zeolite membrane 12 is stably permeable to hydrogen sulfide for a mixed gas, such as biogas, containing hydrogen sulfide (hereinafter, the mixed gas is referred to as a "gas to be separated"). The reasons for this are not clear, but may be inferred as follows.

Since the molecular diameters of nitrogen and hydrogen sulfide are almost the same, the pore size of the zeolite membrane alone is not sufficient for the selective permeation of one from the evaluation gas. Hydrogen sulfide is difficult to permeate through the zeolite membrane because it tends to stay and accumulate in the pores of the zeolite. Therefore, ordinary 8-membered ring zeolite membranes tend to be selectively permeable to nitrogen rather than hydrogen sulfide for the evaluation gas containing nitrogen and hydrogen sulfide. On the other hand, in the above zeolite membrane 12 which is selectively permeable to hydrogen sulfide rather than nitrogen for the evaluation gas, hydrogen sulfide is thought to permeate through the zeolite pores without staying in them, and the pores are unlikely to be clogged by hydrogen sulfide. Therefore, stable permeation of hydrogen sulfide can be achieved for the gas to be separated. As a result, it is possible to suppress the reduction of the separation performance of hydrogen sulfide in the long-time use of the zeolite membrane complex 1 in the separation apparatus 2 (see FIG. 4) described later.

The zeolite membrane 12 that is selectively permeable to hydrogen sulfide rather than nitrogen for the evaluation gas is obtained, for example, by increasing the proton concentration in the membrane above a certain level. This is thought to be because protons do not inhibit the permeation of hydrogen sulfide while interacting moderately with hydrogen sulfide. The previously described temperature-programmed desorption of ammonia measurement can be used to evaluate the proton concentration in the zeolite membrane 12. If the amount of desorbed ammonia in the peak temperature range is, for example, 1 µmol/cm$^3$ or more, the proton concentration in the membrane is somewhat higher, resulting in the zeolite membrane 12 that is selectively permeable to hydrogen sulfide rather than nitrogen. If the amount of desorbed ammonia in the peak temperature range is, for example, 100 µmol/cm$^3$ or less, the proton concentration in the membrane is not too high, resulting in the zeolite membrane 12 with a high permeance of hydrogen sulfide.

Furthermore, in the zeolite membrane 12, the ratio of alkali metal atoms to oxygen atoms in the membrane is preferably 1 atm % or less. This is thought to be because alkali metal ions strongly interact with hydrogen sulfide, and an excess of alkali metal ions in the membrane inhibits the permeation of hydrogen sulfide. In other words, if there are fewer alkali metal ions, the inhibition of the permeation of hydrogen sulfide is suppressed.

Figure 3:
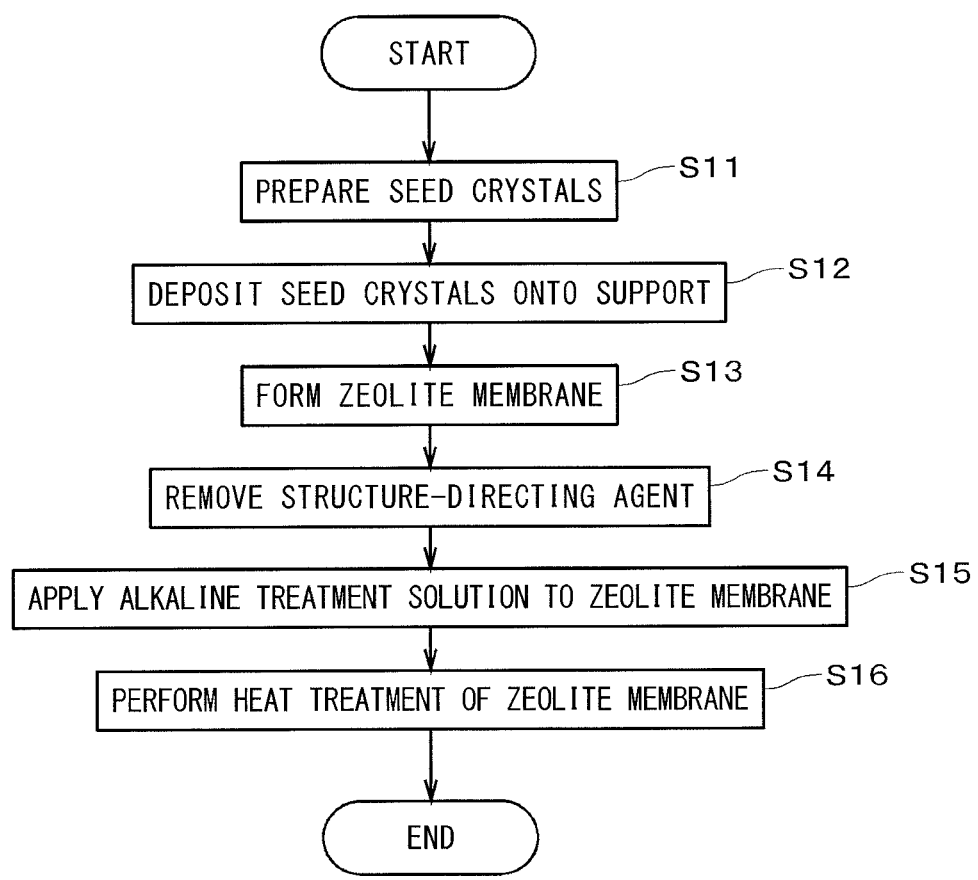
FIG. 3 is a flowchart of production of the zeolite membrane complex.

Next, an example of the procedure for producing the zeolite membrane complex 1 will be described with reference to FIG. 3. The production of the zeolite membrane complex 1 in FIG. 3 is also the production of the zeolite membrane 12. In the production of the zeolite membrane complex 1, first, seed crystals for use in the formation of the zeolite membrane 12 are prepared (step S11). In an example of forming a DDR-type zeolite membrane 12, the seed crystals are, for example, acquired from DDR-type zeolite powder generated by hydrothermal synthesis. This zeolite powder may be used as-is as seed crystals, or may be processed into seed crystals by, for example, pulverization.

Then, the porous support 11 is immersed in a dispersion liquid in which the seed crystals are dispersed, so that the seed crystals are deposited on the support 11 (step S12). Alternatively, a dispersion liquid in which the seed crystals are dispersed may be brought into contact with a portion of the support 11 on which the zeolite membrane 12 is desired to be formed, so that the seed crystals are deposited on the support 11. In this way, a seed-crystal-deposited support is prepared. The seed crystals may be deposited by other methods on the support 11.

The support 11 with the seed crystals deposited thereon is immersed in a starting material solution. The starting material solution is prepared by, for example, dissolving or dispersing starting materials of the zeolite membrane 12, SDA, and the like in a solvent. In an example of forming a DDR-type zeolite membrane 12, the starting material solution contains Si source, SDA, and water as the solvent. The starting material solution may contain other starting materials such as Al source, and the composition of the DDR-type zeolite membrane 12 can be adjusted by, for example, adjusting the composition ratio in the starting material solution. The solvent in the starting material solution may, for example, be a water-insoluble solvent or water-soluble solvent such as alcohol. The SDA contained in the starting material solution may, for example, be an organic substance (organic SDA). As the SDA, for example, 1-adamantanamine or ethylenediamine may be used.

Then, zeolite is grown by hydrothermal synthesis from the seed crystals on the support 11 as nuclei, to form a zeolite membrane 12 composed of an 8-membered ring zeolite on the support 11 (step S13). The temperature of the hydrothermal synthesis is, for example, in the range of 110 to 200° C. The hydrothermal synthesis time is, for example, in the range of 5 to 100 hours.

After the hydrothermal synthesis is completed, the support 11 and the zeolite membrane 12 are rinsed with pure water. After the rinsing, the support 11 and the zeolite membrane 12 are dried at, for example, 100° C. After the support 11 and the zeolite membrane 12 are dried, the zeolite membrane 12 is subjected to heat treatment in an oxidizing gas atmosphere, to thereby burn and remove the SDA in the zeolite membrane 12 (step S14). This allows micropores in the zeolite membrane 12 to come through the membrane. Preferably, the SDA is removed substantially completely. The heating temperature at the time of the removal of the SDA is, for example, in the range of 400 to 1000° C., preferably in the range of 400 to 900° C., and more preferably in the range of 450 to 800° C. The heating time is, for example, in the range of 10 to 200 hours. The oxidizing gas atmosphere is an atmosphere containing oxygen, e.g., in the air.

An alkali source is then dissolved in water to prepare an alkaline treatment solution. As the alkali source, for example, organic amine or quaternary ammonium hydroxide can be used. The pH of the alkaline treatment solution is, for example, in the range of 9.5 to 12, preferably in the range of 10 to 12, and more preferably in the range of 10 to 11.5. With use of the alkaline treatment solution, removal of alkali metal as described later can be performed more effectively.

The alkaline treatment solution is substantially free of ammonium ions ($NH_4^+$). If the treatment solution contains ammonium ions, the permeance of the zeolite membrane 12 may decrease because ammonium ions penetrate into the pores of the zeolite of the zeolite membrane 12. To completely remove ammonium ions from the zeolite membrane 12, heating at a temperature higher than 500° C. (e.g., 600° C.) is required, and thermal damage (e.g., defects) may reduce the separation performance of the zeolite membrane 12. Therefore, alkali sources that produce ammonium ions, such as ammonia, are not suitable. The expression that the alkaline treatment solution is substantially free of ammonium ions means that the concentration of ammonium ions in the alkaline treatment solution is 1 µmol/L or less. The aforementioned ammonium ions do not include organic ammonium ions. This is because organic ammonium ions are large in size and have difficulty penetrating into the zeolite pores.

For the removal of alkali metals from zeolite powder, an aqueous solution of inorganic ammonium salt such as ammonium nitrate or ammonium chloride is used as a treatment solution. However, because the inorganic ammonium salt solution is acidic or neutral, unlike the case of zeolite powder, it is difficult to effectively remove alkali metals from the zeolite membrane 12. In addition, since the inorganic ammonium salt solution contains ammonium ions, the ammonium ions penetrate into the pores of the zeolite membrane 12 when the inorganic ammonium salt solution is used as a treatment solution, as described above. As a result, the amount of desorbed ammonia cannot become 1 µmol/$cm^3$ or more in the temperature-programmed desorption of ammonia measurement described later.

The alkaline treatment solution may contain alkali metals as impurities. The amount of the alkali metals contained in the alkaline treatment solution is preferably small. The concentration of alkali metal ions in the alkaline treatment solution is preferably 0.1 mol/L or less, and more preferably 0.05 mol/L or less. The concentration of alkali metal ions can be determined, for example, by inductively coupled plasma (ICP) emission spectrometry. If the alkaline treatment solution contains a plurality of types of alkali metal ions, the above concentration of alkali metal ions is the total concentration of the plurality of types of alkali metal ions.

After the alkaline treatment solution is prepared, the support 11 and the zeolite membrane 12 are immersed in a sufficient amount of the alkaline treatment solution for one hour or more (step S15). By immersion in the alkaline treatment solution containing, for example, 1-adamantanamine or the like for one hour or more, the alkali metal ions in the zeolite membrane 12 are slowly replaced with hydronium ions, and the alkali metals are removed from the zeolite membrane 12. In other words, an immersion time of less than one hour may not be sufficient to remove alkali metals from the zeolite membrane 12. In the method of applying the alkaline treatment solution to the surface of the zeolite membrane 12 instead of the immersion, a sufficient amount of the alkaline treatment solution cannot be brought into contact with the zeolite membrane 12, which may result in insufficient removal of alkali metals. The immersion time is, for example, in the range of 1 to 100 hours, preferably in the range of 2 to 50 hours. The alkaline treatment solution is preferably heated, which promotes the replacement of alkali metal ions with hydronium ions. The heating temperature is, for example, in the range of 60 to 250° C., and preferably in the range of 80 to 200° C.

In order to reduce dissolution of the zeolite in the zeolite membrane 12 during treatment with the alkaline treatment solution (alkali treatment), the alkaline treatment solution preferably contains at least one of silicon and aluminum, or both silicon and aluminum. The total concentration of silicon and aluminum atoms in the alkaline treatment solution (when only one of silicon and aluminum is contained, it is the atomic concentration of the one; hereinafter the same applies) is, for example, 0.001 mol/L or more, preferably 0.002 mol/L or more, and more preferably 0.005 mol/L or more. In order to suppress the reduction of the permeance of the zeolite membrane 12, the total concentration of silicon and aluminum atoms in the alkaline treatment solution is preferably less than the concentration (i.e., the total concentration of silicon and aluminum atoms) in the starting material solution used to synthesize the zeolite membrane 12 and 1 mol/L or less.

The support 11 and the zeolite membrane 12 are then rinsed with pure water. After the rinsing, the support 11 and the zeolite membrane 12 are dried at, for example, 100° C. After the support 11 and the zeolite membrane 12 are dried, the zeolite membrane 12 is subjected to heat treatment in air (Step S16). This removes adsorbed water and other substances in the zeolite membrane 12, and the hydronium ions are converted to protons. The heating temperature is, for example, in the range of 300 to 500° C., and preferably in the range of 350 to 500° C. The heating time is, for example, in the range of 10 to 100 hours, and preferably in the range of 15 to 50 hours. Through the above-described processing, the zeolite membrane 12 which is selectively permeable to hydrogen sulfide rather than nitrogen for the evaluation gas containing nitrogen and hydrogen sulfide is obtained, and the zeolite membrane complex 1 is completed.

In the above alkali treatment, the zeolite membrane 12 is immersed in the alkaline treatment solution together with the support 11. Alternatively, for example, the method of pouring and holding the alkaline treatment solution only in the through holes 111 to bring the alkaline treatment solution into contact with the zeolite membrane 12 can also be used as an immersion method. Thus, in alkali treatment, the zeolite membrane 12 may be immersed in the alkaline treatment solution by various methods.

As described above, the zeolite membrane complex 1 includes the zeolite membrane 12 composed of an 8-membered ring zeolite, and the zeolite membrane 12 is selectively permeable to hydrogen sulfide rather than nitrogen for the evaluation gas containing nitrogen and hydrogen sulfide. It is therefore possible to provide the zeolite membrane complex 1 that is stably permeable to hydrogen sulfide. As a result, hydrogen sulfide is prevented from accumulating in the zeolite membrane 12 in the separation of hydrogen sulfide from the gas to be separated, and the zeolite membrane complex 1 can be used stably (over a long time) for the separation of hydrogen sulfide.

In temperature-programmed desorption of ammonia measurement for the zeolite membrane 12, an amount of desorbed ammonia in a peak temperature range in which the amount of desorbed ammonia is maximum is 1 µmol/$cm^3$ or more. This makes it possible to reliably achieve the selective permeation of hydrogen sulfide by the zeolite membrane 12. Additionally, in the case where the ratio of alkali metal atoms to oxygen atoms in the zeolite membrane 12 is 1 atm % or less, it is possible to reliably achieve the selective permeation of hydrogen sulfide.

In the production of the zeolite membrane complex 1, the zeolite membrane 12 composed of an 8-membered ring zeolite is formed on the support 11 with use of a starting material solution containing an SDA. Subsequently, the SDA is removed from the zeolite membrane 12. The zeolite membrane 12 is then immersed in an alkaline treatment solution to obtain the zeolite membrane 12 which is selectively permeable to hydrogen sulfide rather than nitrogen for the evaluation gas containing nitrogen and hydrogen sulfide. Thus, the zeolite membrane complex 1 can be produced easily.

The pH of the alkaline treatment solution is in the range of 9.5 to 12, and therefore the zeolite membrane 12 which is selectively permeable to hydrogen sulfide can be produced reliably. The concentration of alkali metal ions in the alkaline treatment solution is 0.1 mol/L or less. This makes it possible to reliably reduce alkali metal atoms contained in the zeolite membrane 12.

The alkaline treatment solution contains at least one of silicon and aluminum, which prevents the zeolite membrane 12 from dissolving in the alkali treatment. The total concentration of silicon and aluminum atoms in the alkaline treatment solution is 0.001 mol/L or more. This reliably prevents the zeolite membrane 12 from dissolving. The total concentration of silicon and aluminum atoms in the alkaline treatment solution is less than the relevant concentration in the starting material solution used to synthesize the zeolite membrane 12 and 1 mol/L or less. This prevents the permeance of the zeolite membrane 12 from being reduced.

Next, an example of producing the zeolite membrane complex 1 will be described.

Example 1

First, DDR-type zeolite powder obtained by hydrothermal synthesis was prepared as seed crystals, and the seed crystals were deposited on the inside of each through hole by bringing the support into contact with a solution where the seed crystals were put into pure water at a predetermined mixing ratio. The mixing ratio was, for example, in the range of 0.001 mass % to 0.36 mass %.

Next, 1-adamantanamine (manufactured by Sigma-Aldrich Co. LLC) as SDA, sodium hydroxide (manufactured by Sigma-Aldrich Co. LLC), 30 mass % colloidal silica (manufactured by Nissan Chemical Corporation: Snowtex S), and sodium aluminate (manufactured by Wako Pure Chemical Industries, Ltd.) were added to pure water (e.g., ion-exchanged water) and mixed, to prepare a starting material solution for a zeolite membrane. The weights of 1-adamantanamine, sodium hydroxide, colloidal silica, sodium aluminate, and pure water at the time of preparing the starting material solution were 1.32 g, 0.35 g, 52.6 g, 0.36 g, and 152.4 g, respectively.

After preparing the starting material solution, the support on which the seed crystals were deposited was immersed in the starting material solution and hydrothermally synthesized at 160° C. for 48 hours, to form a DDR-type zeolite membrane on the support. Then, the support on which the zeolite membrane was formed was thoroughly rinsed with pure water and completely dried at 100° C. Next, the support on which the zeolite membrane was formed was heated in the air at 450° C. for 50 hours so as to burn and remove the SDA, to cause pores in the zeolite membrane to come through the membrane.

Next, 0.31 g of 1-adamantanamine was dissolved in 207 g of pure water, to prepare an alkaline treatment solution. The pH of the prepared alkaline treatment solution was 11. The support on which the zeolite membrane was formed was immersed in the alkaline treatment solution, and the zeolite membrane was alkali-treated by heating at 130° C. for 24 hours. Then, the support on which the alkali-treated zeolite membrane was formed was thoroughly rinsed with pure water and completely dried at 100° C. Next, the support on which the alkali-treated zeolite membrane was formed was heated in the air at 450° C. for 50 hours, to obtain the zeolite membrane complex.

A (hydrogen sulfide)/(nitrogen) separation test was conducted on the zeolite membrane complex of Example 1 using a mixed gas of hydrogen sulfide and nitrogen (1:1 molar ratio), and using a separation apparatus 2 described later. The feed pressure of the mixed gas was 0.9 MPa, the permeate pressure was 0.1 MPa, and the temperature was 25° C. As a result, (hydrogen sulfide permeance)/(nitrogen permeance) was 1.2. Thus, the zeolite membrane complex of Example 1 was found to be a membrane that was selectively permeable to hydrogen sulfide rather than nitrogen.

The temperature-programmed desorption of ammonia measurement was conducted on the zeolite membrane complex of Example 1, and the amount of desorbed ammonia in the peak temperature range was 1 μmol/cm$^3$ or more. The XPS measurement showed that the ratio of alkali metal atoms to oxygen atoms in the zeolite membrane was 1 atm % or less.

Comparative Example 1

The production of zeolite membrane complex of Comparative Example 1 was similar to that in Example 1, except that the operations of the alkali treatment and the subsequent were not performed.

The (hydrogen sulfide)/(nitrogen) separation test was conducted on the zeolite membrane complex of Comparative Example 1 in the same manner as in Example 1, and (hydrogen sulfide permeance)/(nitrogen permeance) was 0.3. Thus, the zeolite membrane complex of Comparative Example 1 was found to be a membrane that was selectively permeable to nitrogen rather than hydrogen sulfide.

The temperature-programmed desorption of ammonia measurement was conducted on the zeolite membrane complex of Comparative Example 1, and the amount of desorbed ammonia in the peak temperature range was less than 1 μmol/cm$^3$. The XPS measurement showed that the ratio of alkali metal atoms to oxygen atoms in the zeolite membrane was greater than 1 atm %.

Comparative Example 2

The production of zeolite membrane complex of Comparative Example 2 was similar to that in Example 1, except that an aqueous solution obtained by dissolving 0.17 g of ammonium nitrate in 207 g of pure water was used instead of the alkaline treatment solution. The pH of the prepared ammonium nitrate solution was 5.6.

The (hydrogen sulfide)/(nitrogen) separation test was conducted on the zeolite membrane complex of Comparative Example 2 in the same manner as in Example 1, and (hydrogen sulfide permeance)/(nitrogen permeance) was 0.5. Thus, the zeolite membrane complex of Comparative Example 2 was found to be a membrane that was selectively permeable to nitrogen rather than hydrogen sulfide.

The temperature-programmed desorption of ammonia measurement was conducted on the zeolite membrane complex of Comparative Example 2, and the amount of desorbed ammonia in the peak temperature range was less than 1 µmol/cm³. The XPS measurement showed that the ratio of alkali metal atoms to oxygen atoms in the zeolite membrane was greater than 1 atm %.

Figure 4:
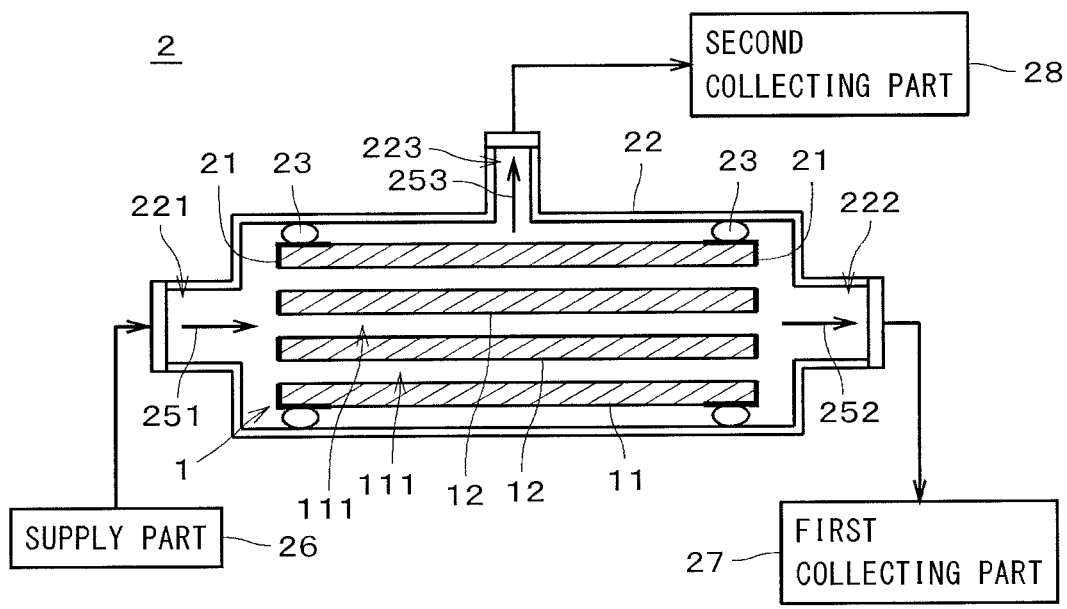
FIG. 4 is a diagram illustrating a separation apparatus.
Figure 5:
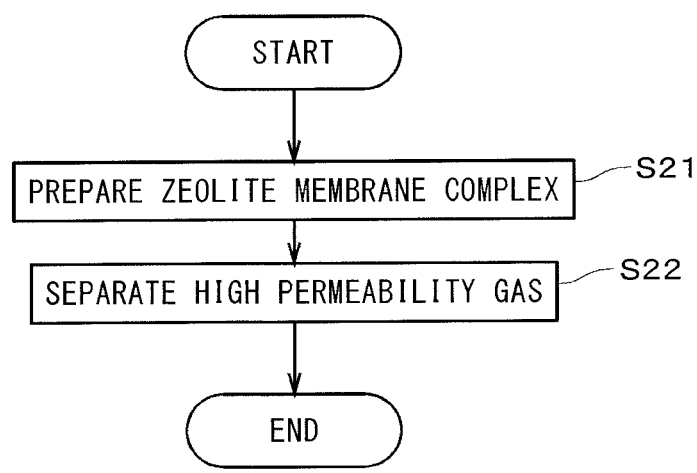
FIG. 5 is a flowchart of separation of a mixed gas by the separation apparatus.

Next, separation of a mixed gas (i.e., gas to be separated) using the zeolite membrane complex 1 will be described with reference to FIGS. 4 and 5. FIG. 4 is a diagram illustrating a separation apparatus 2. FIG. 5 is a flowchart of the separation of the mixed gas performed by the separation apparatus 2.

In the separation apparatus 2, a mixed gas containing a plurality of types of gases is supplied to the zeolite membrane complex 1, a gas with high permeability in the mixed gas permeates through the zeolite membrane complex 1 and that gas is separated from the mixed gas. The separation apparatus 2 is a gas separation apparatus. Separation using the separation apparatus 2 may be performed, for example, in order to extract a gas with high permeability from a mixed gas, or in order to concentrate a gas with low permeability.

As previously described, a typical example of a gas with high permeability in the zeolite membrane complex 1 is hydrogen sulfide ($H_2S$). The mixed gas, which is the gas to be separated, contains at least hydrogen sulfide. The concentration of hydrogen sulfide in the mixed gas may be relatively high, for example, 3 mol % or more. The concentration of hydrogen sulfide in the mixed gas may be even higher (10 mol % or more), but, for example, 50 mol % or less. The concentration of hydrogen sulfide in the mixed gas can be measured, for example, by a commercially available hydrogen sulfide densitometer. The mixed gas may further contain other gases with high permeability.

In the zeolite membrane complex 1, gases with low permeability are not limited. One preferred example of gases with low permeability is hydrocarbons. In other words, the preferred mixed gas further contains hydrocarbons. For example, the mixed gas contains any of C1 to C8 hydrocarbons. The C1 to C8 hydrocarbons are hydrocarbons with one or more and eight or less carbon atoms. The C3 to C8 hydrocarbons may be any one of a linear-chain compound, a side-chain compound, and a ring compound. Further, the C2 to C8 hydrocarbons may either be a saturated hydrocarbon (i.e., in which there is no double bond and triple bond in a molecule), or an unsaturated hydrocarbon (i.e., in which there is a double bond and/or a triple bond in a molecule). The C1 to C4 hydrocarbons are, for example, methane ($CH_4$), ethane ($C2H_6$), ethylene ($C_2H_4$), propane ($C_3H_8$), propylene ($C_3H_6$), normal butane ($CH_3(CH_2)_2CH_3$), isobutane ($CH(CH_3)_3$), 1-butene ($CH_2\!=\!CHCH_2CH_3$), 2-butene ($CH_3CH\!=\!CHCH_3$), or isobutene ($CH_2\!=\!C(CH_3)_2$).

The separation apparatus 2 includes the zeolite membrane complex 1, a sealing part 21, a housing 22, two seal members 23, a supply part 26, a first collecting part 27, and a second collecting part 28. The zeolite membrane complex 1, the sealing part 21, and the seal members 23 are placed in the housing 22. The supply part 26, the first collecting part 27, and the second collecting part 28 are disposed outside the housing 22 and connected to the housing 22.

The sealing part 21 is members mounted on both ends of the support 11 in the longitudinal direction (i.e., left-right direction in FIG. 4) and for covering and sealing both end faces of the support 11 in the longitudinal direction and portions of the outer peripheral face in the vicinity of the end faces. The sealing part 21 prevents the inflow and outflow of gases through the end faces of the support 11. The sealing part 21 is, for example, plate-like members formed of glass or a resin. The material and shape of the sealing part 21 may be appropriately changed. Since the sealing part 21 has a plurality of openings that overlap the through holes 111 of the support 11, both ends of each through hole 111 of the support 11 in the longitudinal direction are not covered by the sealing part 21. This allows the inflow and outflow of gases or the like into/from the through holes 111 through both the ends.

Although there is no particular limitation on the shape of the housing 22, the housing 22 is, for example, a tubular member having a substantially circular cylindrical shape. The housing 22 is formed of, for example, stainless steel or carbon steel. The longitudinal direction of the housing 22 is substantially parallel to the longitudinal direction of the zeolite membrane complex 1. One end of the housing 22 in the longitudinal direction (i.e., left-side end in FIG. 4) has a supply port 221, and the other end thereof has a first exhaust port 222. A peripheral face of the housing 22 has a second exhaust port 223. The supply port 221 is connected to the supply part 26. The first exhaust port 222 is connected to the first collecting part 27. The second exhaust port 223 is connected to the second collecting part 28. The internal space of the housing 22 is a sealed space isolated from the space around the housing 22.

The two seal members 23 are disposed around the entire circumference between the outer peripheral face of the zeolite membrane complex 1 and the inner peripheral face of the housing 22 in the vicinity of both ends of the zeolite membrane complex 1 in the longitudinal direction. Each seal member 23 is a substantially circular ring-shaped member formed of a material impermeable to gases. For example, the seal members 23 are O-rings formed of a resin having flexibility. The seal members 23 are in tight contact with the outer peripheral face of the zeolite membrane complex 1 and the inner peripheral face of the housing 22 around the entire circumference. In the example illustrated in FIG. 4, the seal members 23 are in tight contact with the outer peripheral face of the sealing part 21 and are indirectly in tight contact with the outer peripheral face of the zeolite membrane complex 1 via the sealing part 21. The part between the seal member 23 and the outer peripheral face of the zeolite membrane complex 1 and the part between the seal member 23 and the inner peripheral face of the housing 22 are sealed so as to almost or completely disable the passage of gases.

The supply part 26 supplies a mixed gas to the internal space of the housing 22 through the supply port 221. For example, the supply part 26 is a blower or pump that feeds the mixed gas toward the housing 22 by pressure-feeding. The blower or pump includes a pressure regulator that regulates the pressure of the mixed gas supplied to the housing 22. The first collecting part 27 and the second collecting part 28 are, for example, reservoirs that store gases derived from the housing 22, or blowers or pumps that feed gases.

In the separation of a mixed gas, the aforementioned separation apparatus 2 is provided to prepare the zeolite membrane complex 1 (step S21). Then, a mixed gas containing a plurality of types of gases having different permeability to the zeolite membrane 12 is supplied from the supply part 26 to the internal space of the housing 22. The pressure (i.e., feed pressure) of the mixed gas supplied from the supply part 26 into the internal space of the housing 22 is in the range of, for example, 0.1 MPa to 20.0 MPa. The temperature for separation of the mixed gas is in the range of, for example, 10° C. to 150° C.

The mixed gas supplied from the supply part 26 into the housing 22 is introduced from the left end of the zeolite membrane complex 1 in the drawing into each through hole 111 of the support 11 as indicated by an arrow 251. A gas having high permeability (in a typical example, hydrogen sulfide; hereinafter referred to as a "high permeability gas") in the mixed gas permeates through the zeolite membrane 12 provided on the inner surface of each through hole 111 and the support 11, and is led out from the outer peripheral face of the support 11. In this way, the high permeability gas is separated from a gas having low permeability (e.g., methane; hereinafter referred to as a "low permeability gas") in the mixed gas (step S22). A gas (hereinafter referred to as a "permeate gas") led out from the outer peripheral face of the support 11 is collected by the second collecting part 28 through the second exhaust port 223 as indicated by an arrow 253. The pressure (i.e., permeate pressure) of the gas collected by the second collecting part 28 through the second exhaust port 223 is, for example, approximately one atmospheric pressure (0.101 MPa).

In the mixed gas, a gas (hereinafter, referred to as "non-permeate gas") other than the gas that has permeated through the zeolite membrane 12 and the support 11 passes through each through hole 111 of the support 11 from the left side to the right side in the drawing and is collected by the first collecting part 27 through the first exhaust port 222 as indicated by an arrow 252. The pressure of the gas collected by the first collecting part 27 through the first exhaust port 222 is, for example, substantially the same pressure as the feed pressure. In addition to the aforementioned low permeability gas, the non-permeate gas may also include the high permeability gas that has not permeated through the zeolite membrane 12. The non-permeate gas collected by the first collecting part 27 may, for example, be circulated to the supply part 26 and resupplied into the housing 22.

A (hydrogen sulfide)/(methane) separation test was conducted on the zeolite membrane complex of Example 1 using a mixed gas of hydrogen sulfide and methane (1:1 molar ratio), and using the separation apparatus 2. The feed pressure of the mixed gas was 0.9 MPa, the permeate pressure was 0.1 MPa, and the temperature was 25° C. As a result, (hydrogen sulfide permeance)/(methane permeance) was 5.3. The value of (hydrogen sulfide permeance)/(methane permeance) remained nearly constant during the separation test for more than 5 hours. Thus, the zeolite membrane complex of Example 1 was found to be a membrane that was stably permeable to hydrogen sulfide. On the other hand, when the (hydrogen sulfide)/(methane) separation test was conducted on the zeolite membrane complexes of Comparative Examples 1 and 2, the value of (hydrogen sulfide permeance)/(methane permeance) decreased gradually according to test time.

As described above, in the separation apparatus 2 shown in FIG. 4, the high permeability gas (i.e., hydrogen sulfide) is separated from the mixed gas using the zeolite membrane complex 1 that is selectively permeable to hydrogen sulfide. It is therefore possible to suppress the reduction of the separation performance of hydrogen sulfide due to the accumulation of hydrogen sulfide in the membrane, in the long-time use of the zeolite membrane complex 1 in the separation apparatus 2. As a result, the low permeability gas (e.g., methane) can be stably concentrated. Even when the concentration of hydrogen sulfide in the mixed gas is relatively high (e.g., 3 mol % or more), the separation apparatus 2 can appropriately separate hydrogen sulfide from the mixed gas.

In the zeolite membrane complex 1, the method of producing the zeolite membrane complex 1, the separation apparatus 2, and the separation method described above, various modifications can be made.

In the production of the zeolite membrane complex 1, the process of depositing the seed crystals on the support 11 (FIG. 3: steps S11, S12) may be omitted, and the zeolite membrane 12 may be directly formed on the support 11 in step S13. On the other hand, in order to easily form a zeolite membrane 12 with dense zeolite crystal grains, it is preferable to deposit seed crystals on the support 11 before forming the zeolite membrane 12.

The zeolite membrane complex 1 may further include a function layer or a protective layer laminated on the zeolite membrane 12, additionally to the support 11 and the zeolite membrane 12. Such a function layer or a protective layer may be an inorganic membrane such as a zeolite membrane, a silica membrane, a carbon membrane, or the like or an organic membrane such as a polyimide membrane, a silicone membrane, or the like. Further, a substance that is easy to adsorb specific molecules may be added to the function layer or the protective layer laminated on the zeolite membrane 12.

The separation apparatus 2 and the separation method are particularly suitable for the separation of hydrogen sulfide in a mixed gas containing hydrogen sulfide and hydrocarbons, such as biogas, but may also be used for the separation of hydrogen sulfide in a mixed gas containing hydrogen sulfide and other gases, and may also be used for the separation of substance other than biogas.

The configurations of the preferred embodiments and variations described above may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

INDUSTRIAL APPLICABILITY

The zeolite membrane complex according to the present invention can be used as a separation membrane for various substances, an adsorbent membrane for various substances, or the like in various fields in which zeolite is used.

REFERENCE SIGNS LIST

1 Zeolite membrane complex
2 Separation apparatus
11 Support
12 Zeolite membrane
26 Supply part
S11 to S16, S21, S22 Step

The invention claimed is:
1. A zeolite membrane complex, comprising:
a porous support; and
a zeolite membrane provided on said support, said zeolite membrane being composed of an 8-membered ring zeolite, wherein
said zeolite membrane contains protons,
said zeolite membrane is selectively permeable to hydrogen sulfide rather than nitrogen for a gas containing nitrogen and hydrogen sulfide, and
in temperature-programmed desorption of ammonia measurement for said zeolite membrane, an amount of desorbed ammonia in a peak temperature range in which said amount of desorbed ammonia is maximum is 1 μmol/cm³ or more.

2. The zeolite membrane complex according to claim 1, wherein
in said zeolite membrane, a ratio of alkali metal atoms to oxygen atoms is 1 atm % or less.

3. A separation apparatus, comprising:
a housing comprising said zeolite membrane complex according to claim 1; and
a supply part configured to supply a mixed gas containing at least hydrogen sulfide to said housing.

4. The separation apparatus according to claim 3, wherein said mixed gas contains a hydrocarbon.

5. The separation apparatus according to claim 3, wherein a concentration of hydrogen sulfide in said mixed gas is 3 mol % or more.

6. A separation method comprising:
providing a housing comprising said zeolite membrane complex according to claim 1;
supplying a mixed gas containing at least hydrogen sulfide to said housing; and
obtaining a permeate gas comprising hydrogen sulfide.

7. The separation method according to claim 6, wherein said mixed gas contains a hydrocarbon.

8. The separation method according to claim 6, wherein a concentration of hydrogen sulfide in said mixed gas is 3 mol % or more.

9. A method of producing a zeolite membrane complex, comprising:
forming a zeolite membrane on a porous support with use of a starting material solution containing a structure-directing agent, said zeolite membrane being composed of an 8-membered ring zeolite;
removing said structure-directing agent from said zeolite membrane; and
immersing said zeolite membrane in a treatment solution for one hour or more to obtain said zeolite membrane complex according to claim 1, said treatment solution being alkaline and substantially free of ammonium ions.

10. The method of producing a zeolite membrane complex according to claim 9, wherein a pH of said treatment solution is in a range of 9.5 to 12.

11. The method of producing a zeolite membrane complex according to claim 9, wherein
a concentration of alkali metal ions in said treatment solution is 0.1 mol/L or less.

12. The method of producing a zeolite membrane complex according to claim 9, wherein
said treatment solution contains at least one of silicon and aluminum.

13. The method of producing a zeolite membrane complex according to claim 12, wherein
a total concentration of silicon and aluminum atoms in said treatment solution is 0.001 mol/L or more, and said total concentration is less than the concentration in said starting material solution and 1 mol/L or less.

14. The method of producing a zeolite membrane complex according to claim 9, wherein
said treatment solution contains organic amine or quaternary ammonium hydroxide.

* * * * *